US012688941B2

(12) United States Patent
Koh et al.

(10) Patent No.: US 12,688,941 B2
(45) Date of Patent: Jul. 21, 2026

(54) REAL-TIME NEURAL SPIKE DETECTION

(71) Applicant: Neuralink Corp., Fremont, CA (US)

(72) Inventors: Thong-Wei Koh, San Mateo, CA (US); Paul A. Merolla, Redwood City, CA (US); Sonal Pinto, San Bruno, CA (US); Dongjin Seo, San Francisco, CA (US)

(73) Assignee: Neuralink Corp., Fremont, CA (US)

( * ) Notice: Subject to any disclaimer, the term of this patent is extended or adjusted under 35 U.S.C. 154(b) by 1106 days.

(21) Appl. No.: 16/925,152

(22) Filed: Jul. 9, 2020

(65) Prior Publication Data

US 2021/0012909 A1     Jan. 14, 2021

Related U.S. Application Data

(60) Provisional application No. 62/873,625, filed on Jul. 12, 2019.

(51) Int. Cl.
*G16H 70/60*          (2018.01)
*G06F 16/28*          (2019.01)
(Continued)

(52) U.S. Cl.
CPC ........... *G16H 70/60* (2018.01); *G06F 16/285* (2019.01); *G16H 40/67* (2018.01); *G16H 50/20* (2018.01);
(Continued)

(58) Field of Classification Search
None
See application file for complete search history.

(56) References Cited

U.S. PATENT DOCUMENTS 5,995,868 A * 11/1999 Dorfmeister et al.
8,707,734 B2 4/2014 Haque et al.
(Continued)

FOREIGN PATENT DOCUMENTS

EP          0898460 B1     8/2006
JP      2002502270 A     1/2002
(Continued)

OTHER PUBLICATIONS

R. R. Harrison, "A low-power integrated circuit for adaptive detection of action potentials in noisy signals," Proceedings of the 25th Annual International Conference of the IEEE Engineering in Medicine and Biology Society (IEEE Cat. No. 03CH37439), Cancun, Mexico, 2003, pp. 3325-3328 vol. 4 (Year: 2003).*
(Continued)

*Primary Examiner* — Anna Skibinsky
*Assistant Examiner* — Joseph Pulliam
(74) *Attorney, Agent, or Firm* — Oblon, McClelland, Maier & Neustadt, L.L.P.

(57) ABSTRACT

A method is described for real-time detecting and classifying of a characteristic signal, such as a neural spike, and forwarding information for further processing if it meets certain criteria. A system (e.g., an on-chip system implanted in a subject's cranium) receives an electrical biological signal. The system filters the signal to generate a filtered signal and fits the filtered signal to a model. The system identifies a set of fit values based on the model, the set of fit values comprising a plurality of sample amplitude values and a respective plurality of time values. Based on the fit values, the system computes a set of characteristic values. The system compares the characteristic values to a corresponding set of threshold values. Based on the comparison, the system determines whether the received biological signal (Continued)

corresponds to a neural spike and, if a spike is detected, forwards on information.

15 Claims, 13 Drawing Sheets

(51) Int. Cl.

| | | |
|---|---|---|
| *G16H 40/67* | (2018.01) | |
| *G16H 50/20* | (2018.01) | |
| *G16H 50/70* | (2018.01) | |

(52) U.S. Cl.

CPC ......... *G16H 50/70* (2018.01); *G08C 2201/00* (2013.01)

(56) References Cited

U.S. PATENT DOCUMENTS

| | | |
|---|---|---|
| 2006/0167369 A1 | 7/2006 | Montgomery, Jr. et al. |
| 2009/0124919 A1 | 5/2009 | Ginosar et al. |
| 2012/0275292 A1 | 11/2012 | Micu et al. |
| 2013/0144564 A1 | 6/2013 | Devaul et al. |
| 2016/0213268 A1 | 7/2016 | Kim et al. |
| 2020/0085375 A1 | 3/2020 | Tolosa et al. |
| 2020/0086111 A1 | 3/2020 | Young et al. |

FOREIGN PATENT DOCUMENTS

| | | |
|---|---|---|
| JP | 2004305704 A | 11/2004 |
| JP | 2006271876 A | 10/2006 |
| JP | 2019503746 A | 2/2019 |
| WO | 2018039648 A1 | 3/2018 |

OTHER PUBLICATIONS

Perlin, G. E. (2008). A fully-implantable integrated front-end for neural recording microsystems (Order No. 3343183). Available from ProQuest Dissertations & Theses Global. (304573944). (Year: 2008).*

Nicolelis MA. Actions from thoughts. Nature. Jan. 18, 2001;409(6818):403-7. doi: 10.1038/35053191. (Year: 2001).*

M. M. Maharbiz, R. Muller, E. Alon, J. M. Rabaey and J. M. Carmena, "Reliable Next-Generation Cortical Interfaces for Chronic Brain-Machine Interfaces and Neuroscience," in Proceedings of the IEEE, vol. 105, No. 1, pp. 73-82, Jan. 2017 (Year: 2017).*

PCT/US2020/041372 , "International Preliminary Report on Patentability", Mar. 2021, 4 pages.

Application No. CA3,146,297, Office Action, Mailed On Oct. 6, 2022, 5 pages.

Application No. CA3146297, Notice of Allowance, Mailed On Mar. 20, 2023, 1 page.

Chung et al., A Polymer Probe-Based System for High Density, Long-Lasting Electrophysiological Recordings Across Distributed Neuronal Circuits, http://dx.doi.org/10.1101/242693, Jan. 4, 2018.

P. Merz et al., A Novel Micromachining Technology for Structuring Borosilicate Glass Substrates, Transducers '03, pp. 258-261, Fraunhofer Institute for Silicon Technology (FHG ISIT), Itzehoe, Germany.

A. Tooker et al., "Towards a Large-Scale Recording System: Demonstration of Polymer-Based Penetrating Array for Chronic Neural Recording," 36th Annual International Conference of the IEEE Engineering in Medicine and Biology Society, Aug. 2014, LLNL-CONF-655518, Chicago, IL.

Application No. PCT/US2020/041372, International Search Report and Written Opinion, Mailed On Sep. 24, 2020, 10 pages.

Application No. EP20838873.6, Extended European Search Report, Mailed on Jun. 22, 2023, 9 pages.

* cited by examiner

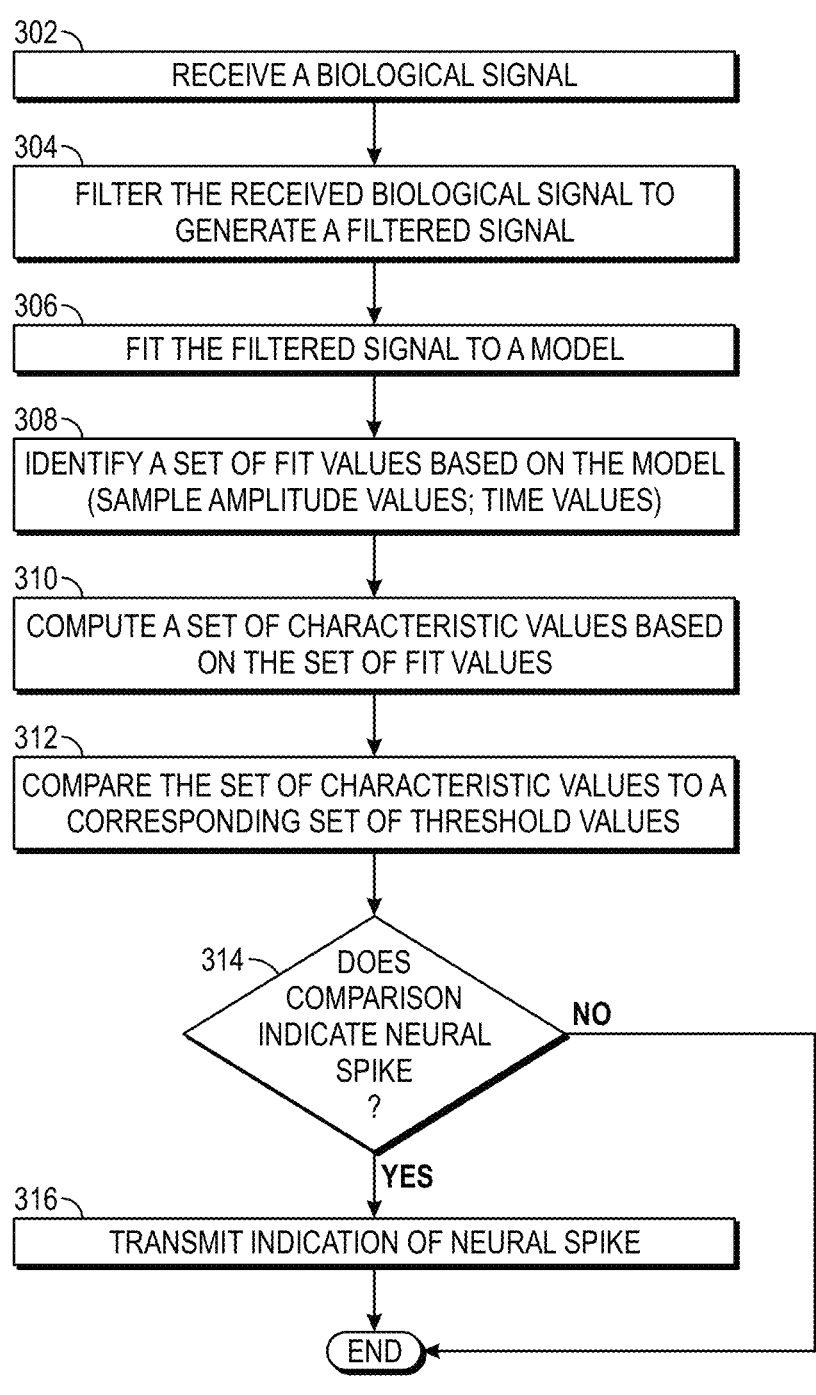

300

302 — RECEIVE A BIOLOGICAL SIGNAL

304 — FILTER THE RECEIVED BIOLOGICAL SIGNAL TO GENERATE A FILTERED SIGNAL

306 — FIT THE FILTERED SIGNAL TO A MODEL

308 — IDENTIFY A SET OF FIT VALUES BASED ON THE MODEL (SAMPLE AMPLITUDE VALUES; TIME VALUES)

310 — COMPUTE A SET OF CHARACTERISTIC VALUES BASED ON THE SET OF FIT VALUES

312 — COMPARE THE SET OF CHARACTERISTIC VALUES TO A CORRESPONDING SET OF THRESHOLD VALUES

314 — DOES COMPARISON INDICATE NEURAL SPIKE ?

NO

YES

316 — TRANSMIT INDICATION OF NEURAL SPIKE

END

REAL-TIME NEURAL SPIKE DETECTION

CROSS-REFERENCES TO RELATED APPLICATIONS

The present application claims the benefit and priority under 35 U.S.C. 119 (e) of U.S. Application No. 62/873,625, filed on Jul. 12, 2019, entitled "NEURAL SPIKE DETECTION," the content of which is herein incorporated by reference in its entirety for all purposes.

FIELD

This application relates to the field of computing devices, signal compression techniques, systems-on-chip, and data traffic flow.

BACKGROUND

There are many applications for retrieving signals characterizing activity in the human brain, such as understanding the workings of the brain and sending signals to control prosthetic limbs.

Key information in a neural signal can be identified based on neural spikes, which are associated with an action potential in a neuron. An action potential, or spike, occurs when a membrane electrical potential rapidly changes. Depolarization and repolarization in the membrane creates a characteristic rise in the voltage across a cell's plasma membrane.

Methods exist for identifying a likely neural spike. Some methods select a likely neural spike based on total voltage exceeding some threshold. This can lead to a surplus of undesirable false positives. Other methods may employ computationally expensive algorithms, such as machine learning, which may consume a great deal of power.

BRIEF SUMMARY

Systems and methods are described for identifying a likely neural spike on-chip in near real-time. Based on the spike detection, the system can compress data received from a biological signal so that useful signals are preserved and extraneous data is not preserved. These techniques are described with respect to a neural signal, although it should be understood that these methods may be useful in other settings, e.g., identifying signature features in other biological signals or electronic signals.

In some embodiments, a system receives a biological signal. The system filters the received biological signal to generate a filtered signal and fits the filtered signal to a model. The system identifies a set of fit values based on the model, the set of fit values comprising a plurality of sample amplitude values and a respective plurality of time values. Based on the set of fit values, the system computes a set of characteristic values. The system compares the set of characteristic values to a corresponding set of threshold values. Based on the comparison, the system determines whether the received biological signal corresponds to a neural spike.

In some embodiments, the method further comprises, based on the comparison, classifying the neural spike as corresponding to a particular spike category, of a plurality of configured spike categories and transmitting output comprising an indicator of the particular spike category and a timestamp.

In some embodiments, the set of fit values comprises: a first sample amplitude value, a second sample amplitude value, a third sample amplitude value, a first time value associated with the first sample amplitude value, a second time value associated with the second sample amplitude value, and a third time value associated with the third sample amplitude value; and the set of characteristic values comprises: a difference between the second time value and the first time value, a difference between the third time value and the second time value, a ratio of the third sample amplitude value and an absolute value of the second sample amplitude value, and a ratio of the first sample amplitude value and the third sample amplitude value.

In some embodiments, the biological signal is received at an input of a chip, the filtering is executed via a bandpass filter comprised in the chip, and the identifying, comparing, and determining are executed via a set of logic gates comprised in the chip.

In some embodiments, the chip is implanted in a cranium of a subject. In some embodiments, the method further includes, based on determining that the received biological signal corresponds to the neural spike, transmitting an indication of the biological signal wirelessly to a receiver external to the cranium of the subject. In some embodiments, the method further includes, based on determining that the received biological signal corresponds to the neural spike, packetizing and transmitting a timestamp corresponding to the biological signal.

In some embodiments, computing the set of characteristic values comprises fixed-point arithmetic calculations. In some embodiments, a first characteristic value, of the set of characteristic values, is assigned a first fixed-point number representation and a second characteristic value, of the set of characteristic values, is assigned a second fixed-point number representation, the number representations being different from each other.

In some embodiments, receiving the biological signal comprises receiving a neural signal via a plurality of electrodes. In some embodiments, determining whether the received biological signal corresponds to the neural spike is executed substantially in real-time.

In some embodiments, a system includes a chip including a plurality of input channels configured to receive a biological signal, a bandpass filter configured to filter the received biological signal to generate a filtered signal, and a controller configured to receive program instructions to fit the filtered signal to a model, identify a set of fit values based on the model, the set of fit values comprising a plurality of sample amplitude values and a respective plurality of time values, based on the set of fit values, compute a set of characteristic values, compare the set of characteristic values to a corresponding set of threshold values, and, based on the comparison, determine whether the received biological signal corresponds to a neural spike.

Some embodiments include non-transitory computer readable media for a method of handling data, the method comprising receiving a biological signal, filtering the received biological signal to generate a filtered signal, fitting the filtered signal to a model, identifying a set of fit values based on the model, the set of fit values comprising a plurality of sample amplitude values and a respective plurality of time values, based on the set of fit values, computing a set of characteristic values, comparing the set of characteristic values to a corresponding set of threshold values, and, based on the comparison, determining whether the received biological signal corresponds to a neural spike.

The foregoing, together with other features and embodiments will become more apparent upon referring to the following specification, claims, and accompanying drawings.

BRIEF DESCRIPTION OF THE DRAWINGS

Illustrative aspects of the present disclosure are described in detail below with reference to the following drawing figures. It is intended that embodiments and figures disclosed herein are to be considered illustrative rather than restrictive.

FIG. 3 is a simplified flowchart illustrating methods for identifying a biological signal in accordance with some embodiments.

DETAILED DESCRIPTION

Figure 1:
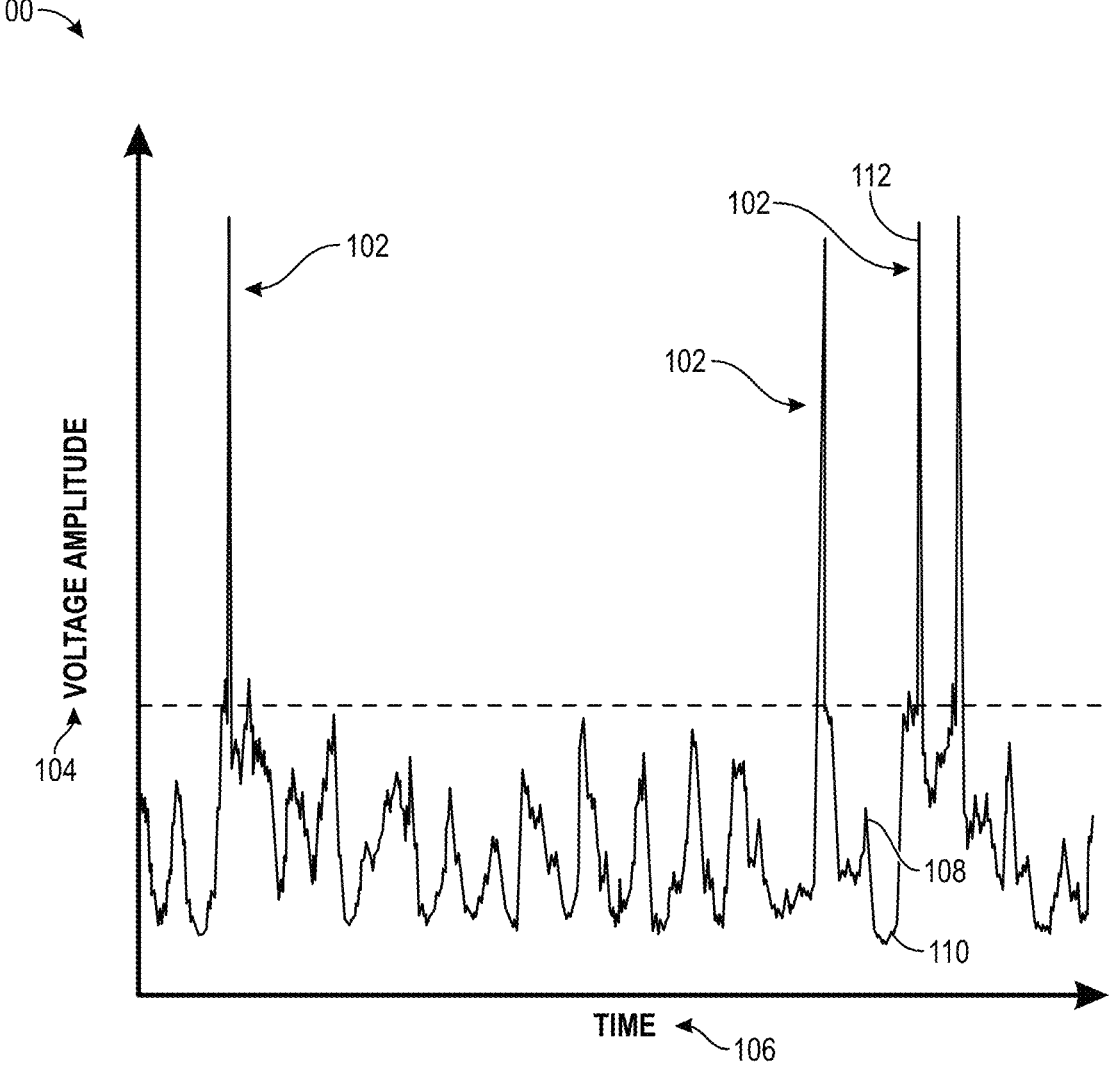
FIG. 1 illustrates example biological signals that can be detected according to some embodiments.

Reference will now be made in detail to embodiments, examples of which are illustrated in the accompanying drawings. In the following detailed description, numerous specific details are set forth in order to provide a sufficient understanding of the subject matter presented herein. But it will be apparent to one of ordinary skill in the art that the subject matter may be practiced without these specific details. Moreover, the particular embodiments described herein are provided by way of example and should not be used to limit the scope of the invention to these particular embodiments. In other instances, well-known data structures, timing protocols, software operations, procedures, and components have not been described in detail so as not to unnecessarily obscure aspects of the embodiments of the invention.

Overview

Brain interfaces with computer systems may require the use of electrodes to receive neurological impulses and turn them into voltage readings or signals. Some example solutions utilize electrodes that contact the outside of the brain or rest on the outside of the skull. Some example solutions utilize electrodes implanted into brain tissue itself. In any arrangement, it may be useful to utilize many different electrodes, placed all over a brain, in order to cover as much of the brain as possible to sense as many neurological readings as possible. There is a need for reliable communication from such electrodes to a computer system for analysis of neurological readings In some example arrangements, electrodes are arranged on a strand or lead and connect to an independent computer chip. The electrodes sense neurological impulses as voltage signals, and pass that information to the chips which handle the data. In one example embodiment, such chips are customized application specific integrated circuit (ASIC) chips which are connected to a strand or strands with electrodes attached to them. These ASIC chips may be referred to as a SoC (system-on-chip) with their own ROM, RAM, EEPROM, flash memory, etc.

These customized ASIC chips may receive and process the voltage readings of the electrodes sensing the neuron signals into data packets for data processing. The chips may then pass the packets along the chip network to ensure each chip sends data on time and send data packets to signal processing on a pin grid array (PGA) board and streamed off to another computing system for analysis and storage.

In some embodiments, thousands of electrodes may be implemented. As the number of electrodes increases, so does the amount of data retrieved, and it becomes increasingly challenging to process and transmit the data on-chip. Thus, it is desirable to extract key information from neural signals, which may be accomplished by isolating data that is likely to correspond to an event of interest, such as a neural spike, from data that can be discarded, such as data retrieved from a neuron at rest and noise. Accordingly, as systems incorporate more and more electrodes, it becomes increasingly important to develop low-power, accurate methods of identifying a neural spike.

Prior techniques for spike detection include thresholding and more complex algorithms such as principal component analysis and machine learning based approaches. In thresholding, data is selected based on a cutoff voltage. Thresholding suffers from false positives, as artifacts such as the subject moving or chewing can create a voltage jump that can be conflated with a biological signal of interest. Principal component analysis and machine-learning based approaches can predict whether a signal corresponds to a spike with good, but not perfect, accuracy. However, such techniques require a relatively large amount of memory and power and would not be practical to implement in an on-chip, implanted system, let alone for real-time online spike detection.

The techniques disclosed herein for some embodiments solve the shortcomings of prior systems by evaluating voltage signals in terms of a simplified shape. A set of features is extracted from a signal—enough to uniquely characterize a biological signal of interest (vs an artifact), without requiring extraneous data storage or processing. This enables the neurological signals to be identified in an online, real-time fashion.

Example Biological Signals

FIG. 1 illustrates an example of a graph 100 of neural voltage over time, including spikes 102 (e.g., neural spikes). Neural spikes are associated with a characteristic change in sample amplitude 104 over time 106. The sample amplitude may, for example, represent voltage, power, or frequency. As a specific example, the sample amplitude 104 is voltage in millivolts (mV).

A spike 102 is preceded by excitation and inhibition of a membrane. Cells such as neurons transport electrical signals using action potentials. An action potential is characterized by a voltage change across a cell membrane due to the flow of ions into and out of the neuron. Membranes are permeable to positively and negatively charged ions. The membranes are generally in a resting state. During depolarization, voltage-gated ion channels open due to an electrical stimulus. As ions rushes back into the cell, the charged ions modify the charge inside the cell (e.g., an influx of positive sodium ions raise the charge inside the cell from negative to positive). If a threshold is reached, then an action potential is produced. Once the cell has been depolarized, the voltage gated ion channels close. As charged ions exit the cell, the membrane potential falls and starts to approach the resting potential. Typically, repolarization overshoots the resting membrane potential, making the membrane potential more negative (hyperpolarization). An action potential is followed by a refractory period.

As illustrated in FIG. 1, a spike 102 can be characterized by characteristic rises and falls in sample amplitude. A signal may start out with an initial resting value, followed by a first positive change in sample amplitude 108, followed by a reduction in sample amplitude 110 below the resting value, and a second positive change in sample amplitude 112. The second positive change in sample amplitude 112 is generally greater than the first positive change in sample amplitude 108. In some embodiments, spikes in a biological signal are viewed in a shape space based on these characteristic changes in sample amplitude over time.

Spike Detection System

Figure 2A:
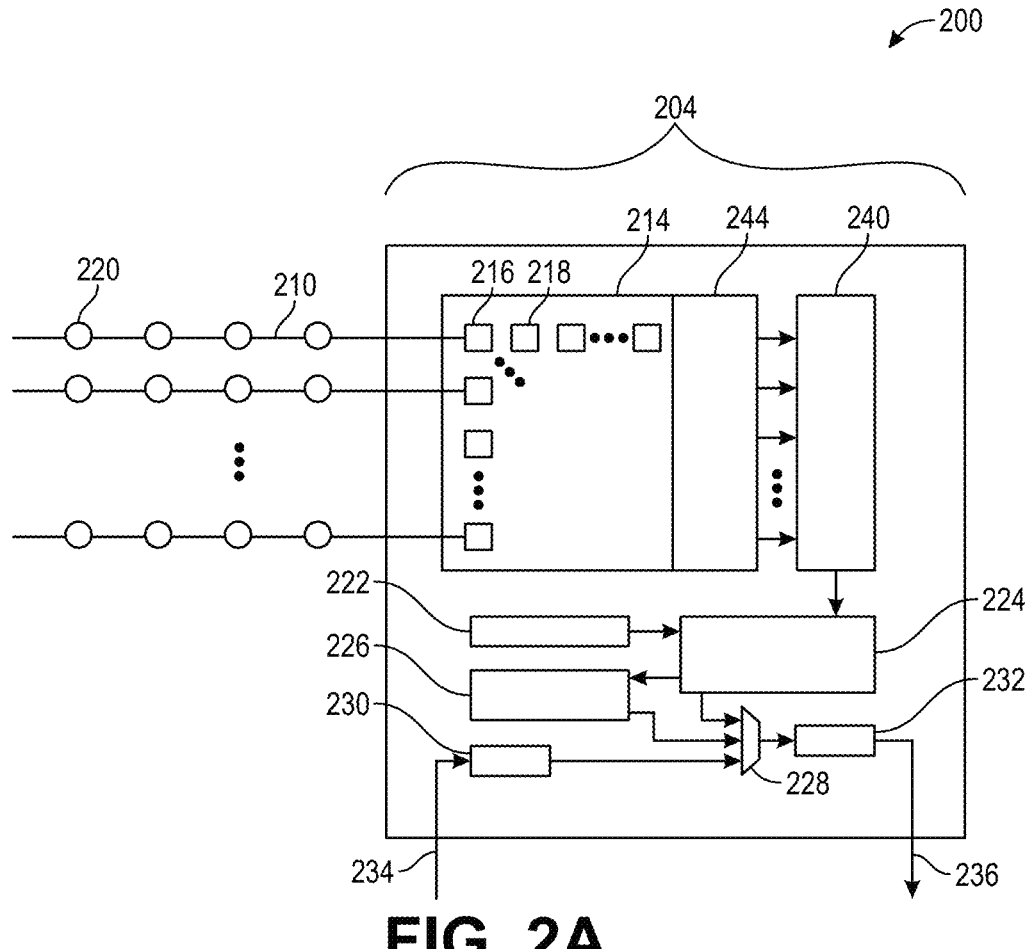
FIG. 2A is a simplified block diagram of a network on chip in accordance with some embodiments.

FIG. 2A illustrates a simplified block diagram of a system 200 for detecting a neural spike in accordance with some embodiments. The system 200 includes a plurality of electrode leads 210 coupled to a chip 204. Each electrode lead 210 includes a plurality of electrodes 220 disposed on the lead. Each electrode 220 senses neurological voltage readings, and passes a voltage signal to the chip 204 via the respective lead 210. Components of chip 204 include amplifiers 214, an analog-to-digital converter (ADC) 244, a multiplexer 240, a controller 224, a configuration circuitry 222, a compression engine 226, a merge circuitry 228, a deserializer 230, and a serializer 232. The chip 204 may digitize, process, and/or packetize neurological readings before sending signal data off the chip 204 to a back end computing system and/or data storage. In some embodiments, the chip includes a wireless transmitter adapted to wirelessly transmit output signal data to a wireless receiver in the back end computing system. In some embodiments, the system 200 may be implanted in a subject (e.g., in a cranium of a subject), and the back-end computing system is external to the cranium of the subject.

It should be known that the circuitry described in the various chip 204 elements herein may be hardware implemented using any number of resistors, capacitors, diodes, leads, busses, memory, ROM, processors, or any other kind of discrete hardware components. In some examples, additionally or alternatively, the circuitry described could be virtualized in a cohesive processor and memory and run as software. Either option may be utilized alone or in combination with each other, although the components described herein are referred to as hardware elements of circuitry.

In some examples, a deserializer 230 on the chip 204 may convert packets from an off-chip serial link to an on-chip network as well as act as a queue for incoming data packets from the input 234. In some examples, a serializer 232 may act as a queue for outbound packets to be sent to other chips 236 or off chip to another computing resource. In some examples, these queues for the deserializer 230 and the serializer 232 are de-coupled and independent and can send/receive/queue without effect on one another.

Data flow within the chip begins upon providing power to the chip 204. The electrodes 220 detect neuron voltage readings within or from the brain itself and pass on the analog voltage signals to the chip 204 by way of one or more amplifiers 216, 218. In the example depicted in FIG. 2A, multiple amplifiers are arranged in an array of amplifiers 214, each in communication with a lead 210 and thereby any number of electrodes 220. This array of amplifiers 214 is configured on the chip 204 to receive analog signal information from the electrodes 220 through a lead 210 and then amplify the signals.

In some embodiments, the one or more amplifiers 216, 218 transmit amplified analog signals which are then sent to the analog-to-digital converter 244 which digitizes the signals from the analog array of amplifiers 214. The analog-to-digital converter may, for example, be a 256 channel multiplexed ADC. The analog-to-digital converter 244 may transmit the digitized signals to a multiplexer 240 for serializing the signals and/or data. Alternatively, or additionally, the digital signals may be analyzed by the system directly.

In some embodiments, the chip 204 includes a configuration circuitry 222, which is a programming interface to the chip from a back-end computing system. The configuration circuitry 222 and back-end computing system can be used to configure the system to operate in a desired mode. For example, as described herein, the spike detection algorithm can be a function of tunable parameters that can be modified after the chip is implanted in a subject.

In some embodiments, data information signals (e.g., data that has been serialized in the multiplexer 240) are sent to the controller 224. The controller 224 is in communication with the compression engine 226 and the merge circuitry 228. The controller 224 creates data packets with the various digitized electrode signal data. Based on the settings/mode set by the configuration circuitry 222, the controller 224 packetizes the data and sends data to the next set of stages/circuitry.

The neurological signal, which may be in analog or digital form, is passed to a compression engine 226 for further processing. The relatively high-bandwidth signals (e.g. 20 kHz sampling) from the array of amplifiers 214 are sent to the compression engine 226 by way of the controller 224. The data received by the compression engine 226 may contain low and high frequency contents of neurological signals. The compression engine 226, using techniques as described further herein, identifies signals likely to correspond to neural spikes, and thereby selects certain signals characteristic of a neural spike to process and certain signals to discard.

In some embodiments, the merge circuitry 228 is configured to and/or programmed to decide which packets to send off chip and when to send those packets, based on its programming. The merge circuitry 228 sends packets off chip through a serializer 232 out to the next chip or to an external computing device.

Figure 2B:
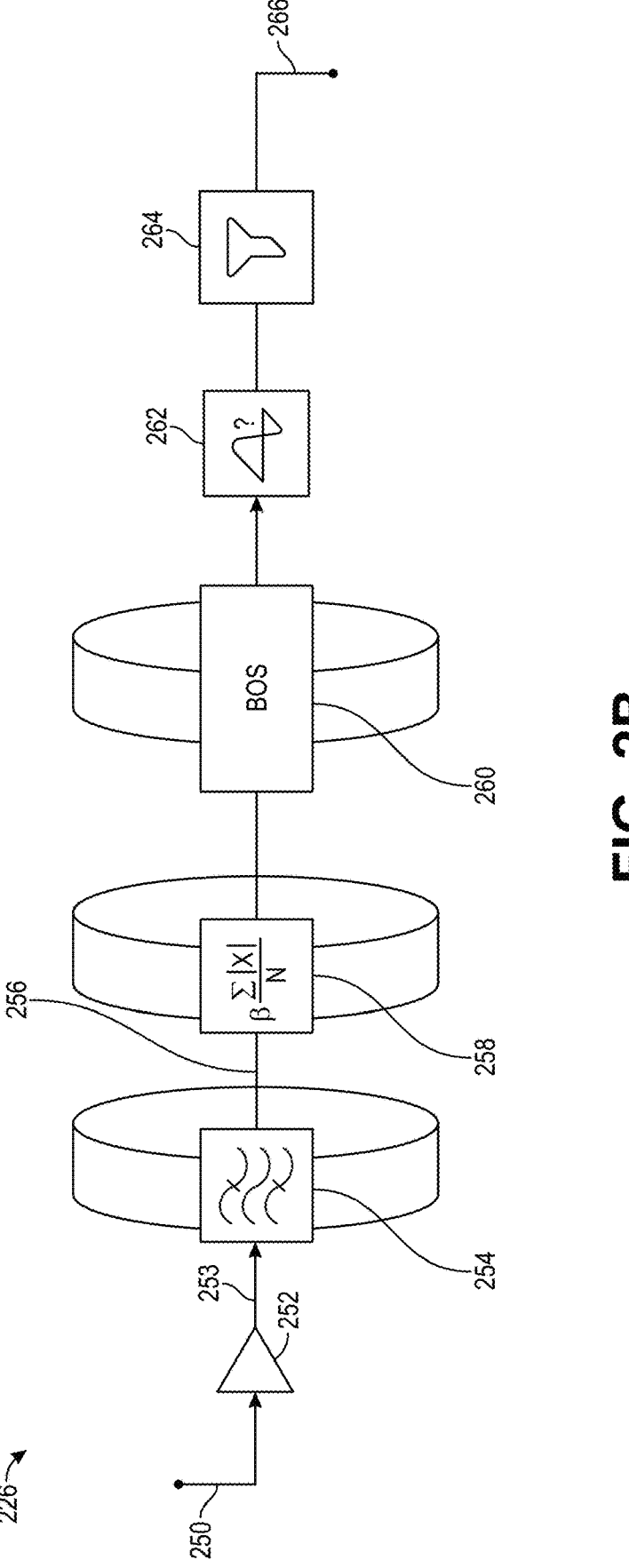
FIG. 2B is a simplified block diagram of components of the network on chip of FIG. 2A for spike identification and signal compression in accordance with some embodiments.

FIG. 2B is a simplified block diagram showing the compression engine 226 in further detail. The compression engine 226 may include an amplifier 252, a bandpass filter 254, a mean absolute deviation (MAD) and threshold calculation subsystem 258, a buffered online spike detector (BOS) subsystem 260, a spike probability evaluation subsystem 262, and a spike classifier subsystem 264.

As described above with respect to FIG. 2A, input 250 to the compression engine 226 may be a digital or analog signal. The signal may originate from a plurality of electrodes coupled to a respective plurality of neurons. In some embodiments, the input 250 may come in via multiple channels. The multiple channels may include thousands or tens of thousands of channels. Input 250 may include 10 bit (b) samples at a sampling rate of approximately 16-20 KHz.

In some embodiments, the received input 250 passes through the amplifier 252. At amplifier 252, the input may be re-scaled. The input 250 may pass through one or more of a low-noise amplifier (e.g., a low-noise neural amplifier) and a variable-gain amplifier. The output of the amplifier 252 is an amplified signal 253.

Figure 9:
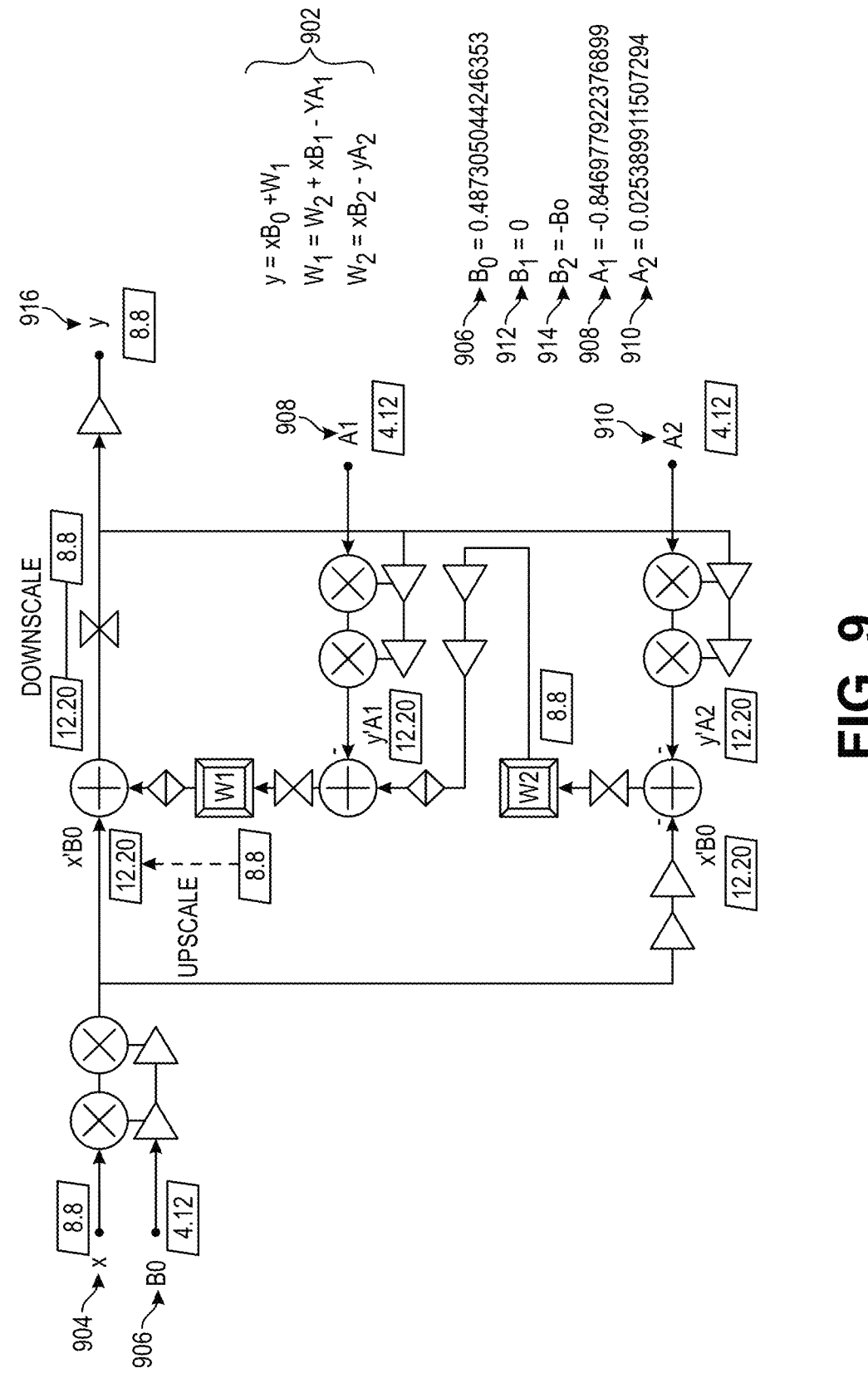
FIG. 9. illustrates a bandpass filter in accordance with some embodiments.

In some embodiments, the amplified signal 253 is transmitted to the bandpass filter 254 for further processing. The bandpass filter 254 may be used to select a subset of frequencies which could correspond to a desired signal (e.g., a neural spike). In some embodiments, the bandpass filter 254 includes a single-port SRAM ring buffer to multiplex evaluation over multiple channels, utilizing 32 b/channel. The bandpass filter may be, for example, a 500 Hz-5 KHz filter, which is suitable to isolate frequencies characteristic of a neural spike. FIG. 9, described below, illustrates such a filter in detail. The bandpass filter 254 generates a filtered signal 256. The filtering may occur in analog or digital.

Mean absolute deviation (MAD) and threshold calculation subsystem 258 may receive the filtered signal 256 and compute a deviation value that is an estimate of the statistical dispersion of a channel. In some embodiments, the deviation value is the mean absolute deviation of the signal. Alternatively, or additionally, the deviation value may be the standard deviation. Computing the mean absolute deviation may preferred in some cases to reduce the processing time and resources in comparison to those used in standard deviation calculations. The MAD and threshold calculation subsystem 258 may further calculate one or more threshold values based upon the deviation value. In some embodiments, the MAD and threshold calculation subsystem 258 includes a single-port SRAM ring buffer to multiplex evaluation over multiple channels, utilizing 22 b/channel. MAD calculation is described in further detail below with respect to FIG. 10.

Figure 4A:
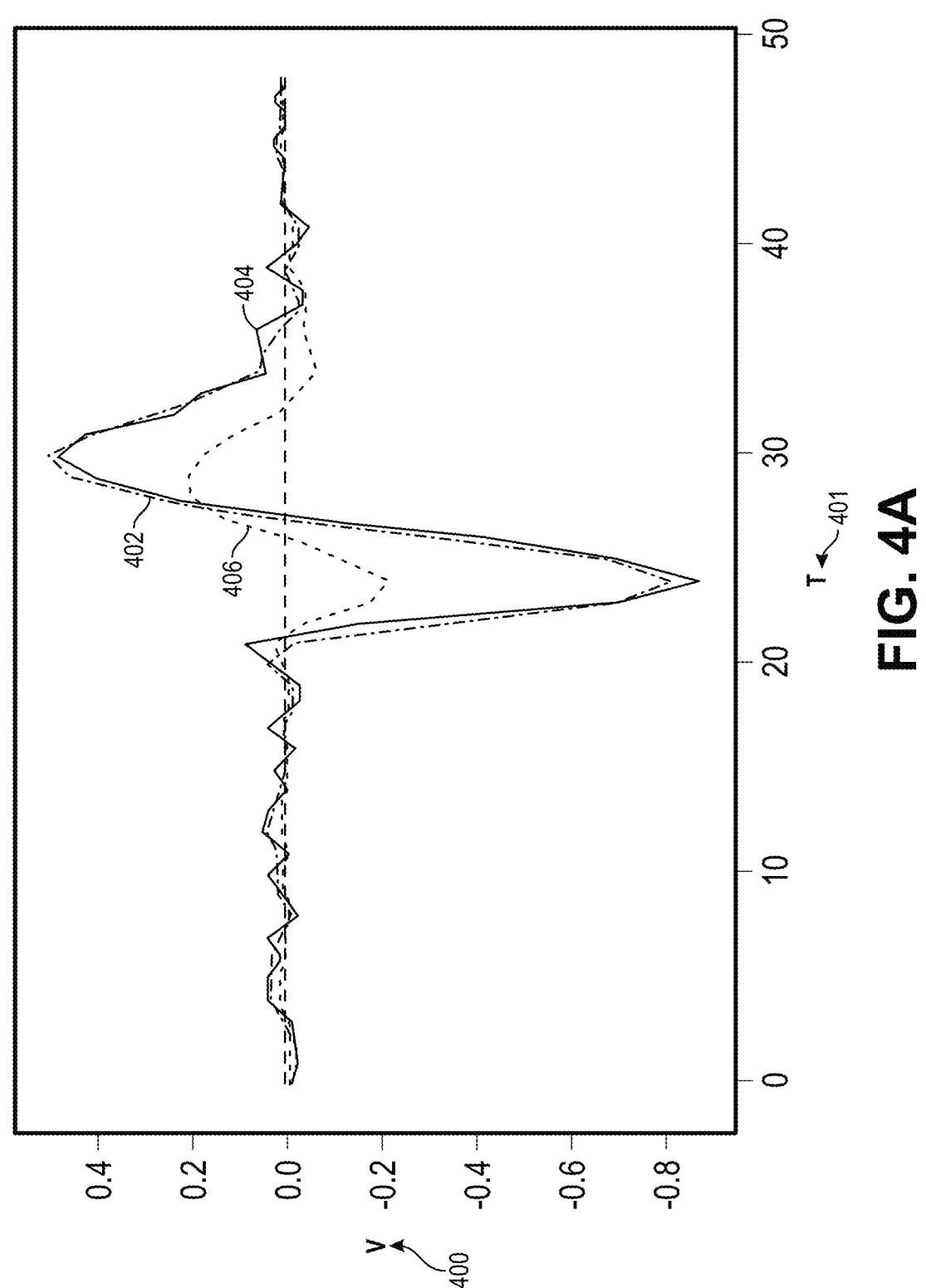
FIG. 4A illustrates smoothing of a biological signal in accordance with some embodiments.
Figure 4B:
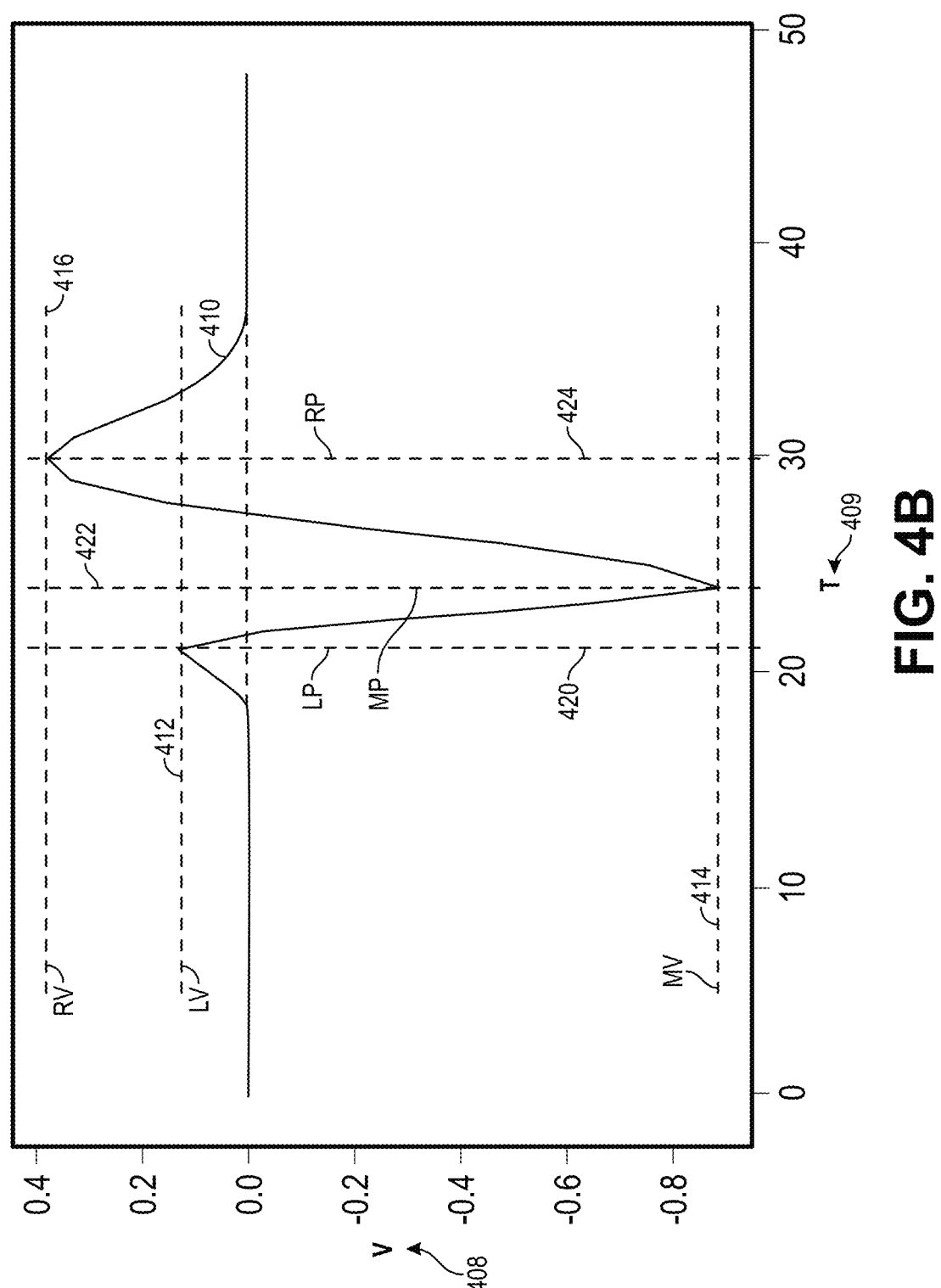
FIG. 4B illustrates identification of a set of fit values from a signal in accordance with some embodiments.

Buffered online spike detector (BOS) subsystem 260 may receive the filtered signal and/or values generated by the MAD and threshold calculation subsystem 258. BOS subsystem 260 analyzes the received signal to identify fit values in the signal (e.g., sample amplitudes and/or times corresponding to signature patterns in the signal, as shown in FIG. 4B). The BOS subsystem 260 may analyze the signal to identify such values, as described in further detail below with respect to FIGS. 4A-4C. The BOS computations may be performed using a ring buffer. In some embodiments, the BOS subsystem includes a single-port SRAM ring buffer to multiplex evaluation over multiple channels, utilizing 172 b/channel (e.g., a single-port 172×256 SRAM ring buffer). The BOS computations are may be performed online by processing the data as it is received. The BOS subsystem 260 may use multiplexed dynamic programming with stored states pipelined for incremental compute and shortening critical path. For example, a first pipeline may detect peaks and a second pipeline may detect valleys. The output of the BOS subsystem 260 may include data that the spike probability evaluation subsystem 262 can further process to evaluate whether data likely corresponds to an event such as a neural spike.

Spike probability evaluation subsystem 262 may use information provided by the BOS subsystem 260 to determine a likelihood that a neural spike is detected. The spike probability evaluation subsystem 262 identifies characteristic values in a signal, and compares them to one or more threshold values. The spike probability evaluation subsystem 262 may, for example, receive identified fit values from the BOS subsystem 260 and use these fit values to compute characteristic values for comparison to the threshold value(s). Based on the comparison, the spike probability evaluation subsystem 262 identifies whether there is sufficient likelihood that the data corresponds to an event of interest (e.g., a neural spike), in order to preserve and/or transmit an indication of the corresponding data. Determining neural spike likelihood is described further below with respect to FIG. 5.

In some embodiments, spike classifier subsystem 264 classifies the spikes and transmit as output sorted spikes 266. The spike classifier subsystem 264 may classify the spikes into different categories based on the values computed by the BOS subsystem 260 and/or spike probability evaluation subsystem 262, as described further below with respect to FIG. 6. In some embodiments, the outputs of the spike detection process are packetized and can be sent out via serial links or wirelessly. Packets can indicate the presence of a spike (time stamped) and may include the estimates of the shape, as well as classifying the shape into distinct categories (spike shape A, B, . . . ). Alternatively, or additionally, in some cases, the spikes are not classified, in which case the system may transmit a timestamp and/or the data corresponding to the detected spike (e.g., the characteristic values and/or a processed signal). If a spike is not detected, then the compression engine 226 may discard or otherwise refrain from transmitting a signal, in order to reduce the amount of network transmissions and power required.

Spike Detection Techniques

FIG. 3 depicts a simplified flowchart illustrating a method 300 for identifying a neural spike according to some embodiments. Although FIG. 3 depicts the various processing steps occurring in a particular sequence or order, this is not intended to be limiting. In certain alternative embodiments, the steps may be performed in some different order or some steps may also be performed in parallel. In certain embodiments, the processing depicted in FIG. 3 may be performed by the compression engine 226 of FIGS. 2A and 2B in cooperation with other components of the system 200 described above with respect to FIGS. 2A and 2B.

At step 302, the system receives a biological signal. A biological signal, such as a neurological voltage signal, may be received. For example, as shown in FIG. 2A, biological signals are fed onto the chip 204 via a plurality of electrode leads 210.

At step 304, the system filters the received biological signal to generate a filtered signal. The biological signal may pass on-chip through a filter, such that a subset of the biological signal of interest is retained. As an example, a high pass filter may be applied to select portions of the biological signal that exceed some threshold voltage. As another example, a bandpass filter may be applied to select portions of the biological signal in a configured voltage band. In some embodiments, a Butterworth filter is applied to select a voltage window, a specific example of which is described in further detail below with respect to FIG. 9.

At step 306, the system fits the filtered signal to a model. In some embodiments, the system fits the filtered signal to a polynomial. In some embodiments, fitting the filtered signal to a model may include or be preceded by applying a local smoothing function, such as Brown's double exponential smoothing function, to the filtered signal, as described in further detail below with respect to FIG. 4A.

At step 308, the system identifies a set of fit values based on the model. The fit values include sample amplitude values and time values. As illustrated in FIG. 4B, the fit values lp, mp, rp, lv, mv, and rv correspond to characteristic features in a plot of sample amplitude as a function of time. In the specific example illustrated in FIG. 4B, there are three sample amplitude values identified, which correspond to local minima and maxima of the curve. A time value corresponding to respective each sample amplitude value is also identified. This example is described in further detail below with respect to FIG. 4B.

In some embodiments, identifying the fit values may be executed by identifying local maxima and minima in a plot of sample amplitude (e.g., voltage) over time. This can be achieved by windowing segments of the plot and identifying a local maximum or minimum in each window. Alternatively, or additionally, the plot of sample amplitude over time can be represented as a mathematical model (e.g., a polynomial model), and the features can be identified based on the polynomial model.

At step 310, the system computes a set of characteristic values based on the set of fit values. Each characteristic value, of the set of characteristic values, is based on one or more of the fit values identified at step 308. For example, one characteristic value is a first time value minus a second time value, and represents the time elapsed between a local maximum and a local minimum in the voltage of the signal over time. Another characteristic value is a first sample amplitude divided by a second sample amplitude, and represents the relative voltage of two features corresponding to the two sample amplitudes. Specific examples of such characteristic values are described in further detail below with respect to FIG. 5.

At step 312, the system compares the set of characteristic values to a corresponding set of threshold values. The system may identify threshold values corresponding to each of the characteristic values. Such threshold values may be stored and/or configurable. For example, four threshold values, corresponding to four respective characteristic values, are tunable parameters stored on-chip. The system compares each characteristic value computed at 310 to a corresponding identified threshold value.

Figure 5:
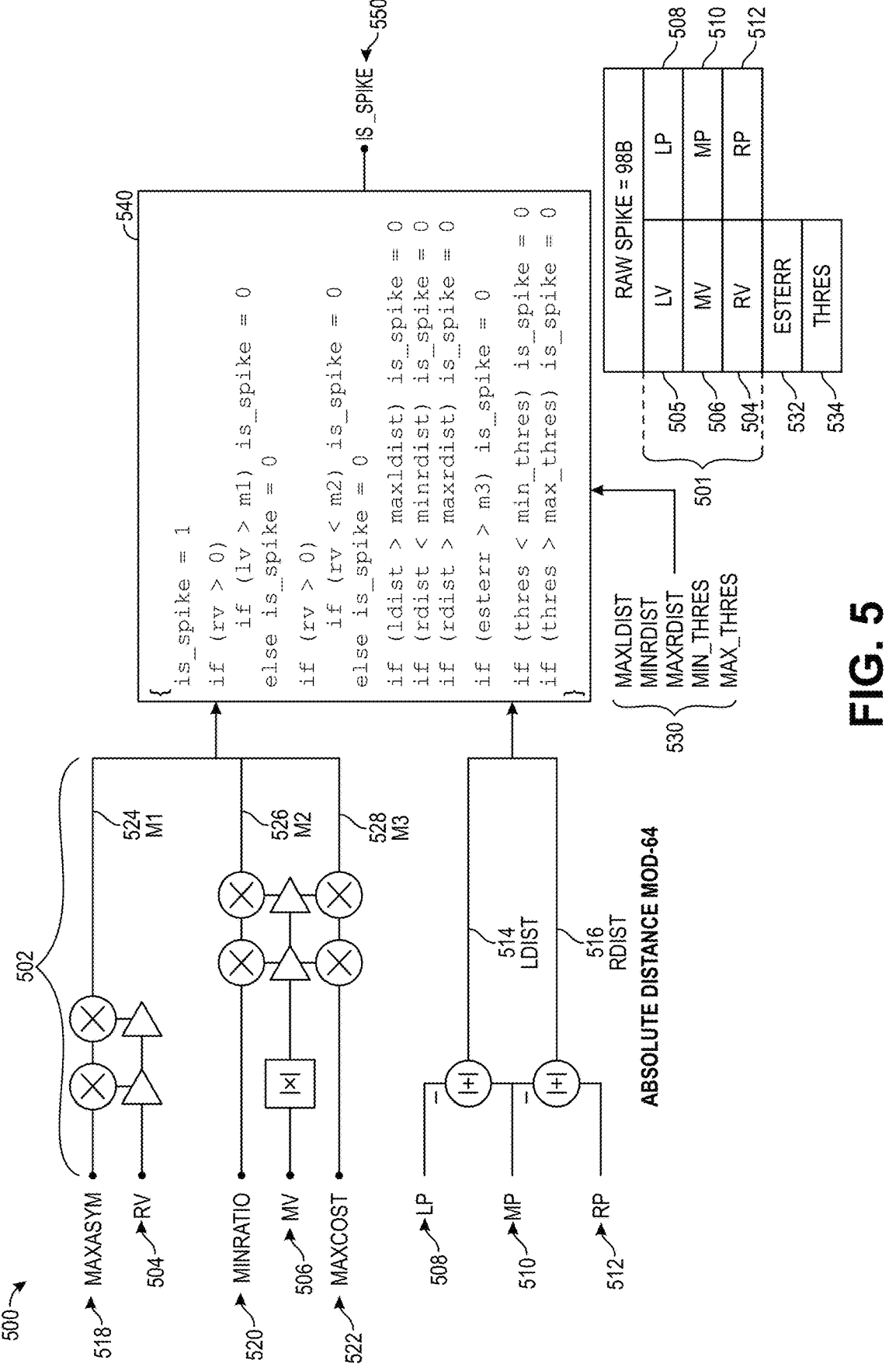
FIG. 5 illustrates techniques for determining whether a neural spike is detected according to some embodiments.

At step 314, the system determines whether the comparison indicates a neural spike. For example, if a first characteristic value exceeds a first threshold value and a second characteristic value is below a second threshold, then the system determines that a detected signal is likely associated with a neural spike. As another example, the system may use logic comprising a set of functions of multiple characteristic values, fit values, and/or threshold values to determine whether a detected signal is likely from a neural spike. An example of such logic 540 is illustrated in FIG. 5.

At step 316, if the comparison at step 312 indicates a neural spike at step 314, then the system transmits an indication of the neural spike. The system may packetize and transmit the indication of the neural spike off-chip. For example, the system transmits the indication of the neural spike from a first chip in a chip network to a second chip in a chip network. As another example, the system transmits the indication of the neural spike from a chip implanted in the cranium of a subject to a computing device external to the cranium of the subject (e.g., via wired connection and/or a wireless transmission).

The indication of the neural spike may take various forms as is suitable in the circumstance. In simple form (which can be suitable to minimize processing resources), the indication may simply be a timestamp indicating the time at which the neural spike was identified and/or a value (e.g., "1") indicating that a neural spike was identified. Accordingly, based on determining that the received biological signal corresponds to a neural spike, the system may packetize and transmit a timestamp corresponding to the biological signal.

Alternatively, or additionally, the system may classify each detected neural spike as corresponding to a particular spike category, of a plurality of configured spike categories. The spikes may be sorted into the different categories based on the characteristic values, as described in further detail below with respect to FIG. 6. In this case, the system may transmit output comprising an indicator of a particular spike category and a timestamp. The indicator of the particular spike category can be a representation of a particular spike category (e.g., 1, 2, 3, 4, for four predefined spike categories; 0-8 for nine predefined spike categories, and so forth). For example, the spikes may be classified based upon the magnitude of one or more voltage values, a time difference between features in the detected signal, or a combination of such factors. By categorizing the spike, valuable information can be retained while still keeping processing resource usage low.

Figure 4C:
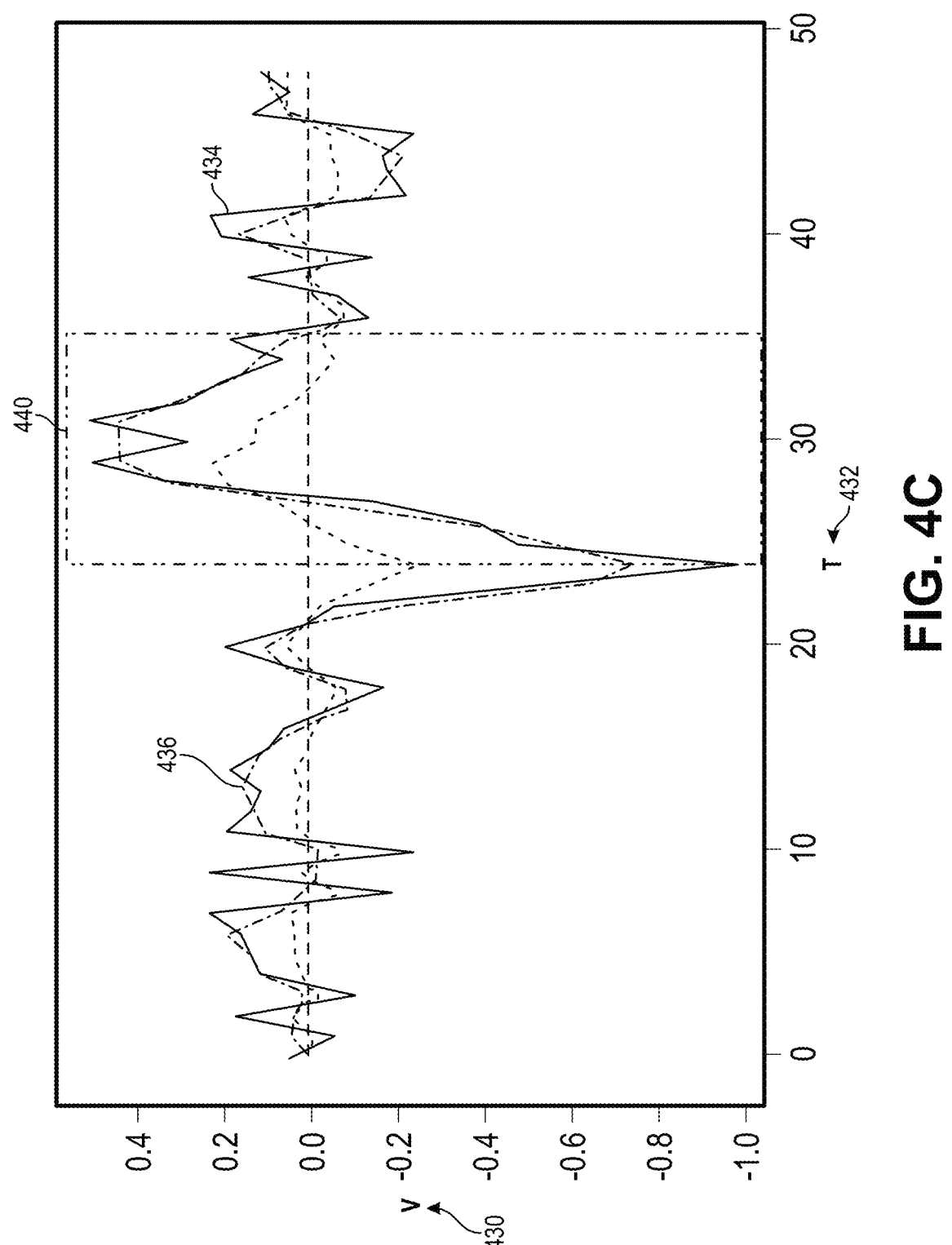
FIG. 4C illustrates analysis of a biological signal in accordance with some embodiments.

As another example, the indication of the neural spike may include the computed characteristic values and/or the identified fit values (e.g., the values and times of local maxima and minima, and/or functions thereof, may be transmitted off chip). The spike detection techniques can return an indication of major characteristics in a signal corresponding to a spike (e.g., approximate distance of the left and right humps from the minimum deflection and the signal levels at the 3 locations). The spike detection techniques may further return a proxy for the noise computed as the total variations against a local smoothing function (e.g., as shown in FIGS. 4A-4C). In some cases, the indication of the neural spike may include the neurological voltage signal itself, in whole or in part. As a specific example, the system can generally transmit a simple indicator (e.g., a timestamp) to indicate a neural spike has been detected. If additional information about the neural spike and/or debugging is desired, then the voltage signal, fit values, and/or characteristic values may be transmitted off chip responsive to a request for additional data.

If the comparison at step 312 does not indicate a neural spike at step 314, then the process ends. The system refrains from transmitting and/or storing the information that does not correspond to a neural spike.

In some embodiments, the spike detection process of FIG. 3 operates on a sample by sample basis, receiving inputs from each of a plurality of channels on the chip in succession. Internal states are kept in circular buffers (e.g., the bandpass filter 254, MAD and threshold calculation subsystem 258, and/or BOS subsystem 260). The internal states stored in the buffers may be flushed on reset for the first frame. Using the buffered online spike detection techniques of FIG. 3, determining whether the received biological signal corresponds to a neural spike is executed substantially in real-time (e.g., in roughly 1 microsecond ($\mu$s) from the receipt of the signal to determination whether a neural spike is detected).

Although the examples described above pertain to neurological voltage signals and neural spikes, the techniques can be applied to other biological signals, such as cardiac voltage signals.

FIGS. 4A-4C illustrate examples of biological signals and processing thereof in accordance with some embodiments. In FIGS. 4A-4C, the y-axis is sample amplitude (specifically, in this example, voltage in mV) and the x-axis is time.

FIG. 4A illustrates smoothing of a biological signal 404 in accordance with some embodiments. The biological signal 404 is represented by time series data of sample amplitude 400 (e.g., voltage V) over time (t) 401. A local smoothing function 402 is used to estimate local maxima and local minima in the biological signal 404. The local smoothing function 402 may also be used to estimate a trend 406 in the data. In some embodiments, the smoothing function is Brown's double exponential smoothing algorithm, as described in Hansun, Seng, "A New Approach of Brown's Double Exponential Smoothing Method in Time Series Analysis," *Balkan Journal of Electrical and Computer Engineering,* 4. 10.17694/bajece.14351 (2016). In some cases, such as for the signal shown in FIG. 4C, an unsmoothed biological voltage signal includes large fluctuations which makes it relatively difficult to identify a shape, fit to a model, or extract features of interest using the signal. Accordingly, smoothing the signal is useful in obtaining the fit values to extract useful information from the signal.

FIG. 4B illustrates identification of a set of fit values from a signal 410 in accordance with some embodiments. The signal 410 is represented by time series data of sample amplitude 408 (e.g., voltage V) over time (t) 409. Three features can be seen in the signal 410: a peak in moderate positive sample amplitude to the left, a relatively large dip in sample amplitude towards the middle, and a relatively large peak in sample amplitude to the right.

As indicated in FIG. 4B, the basic features of the filtered signal 410 can be described with six fit values or outputs—three sample amplitudes and three time values. The sample amplitudes illustrated in FIG. 4B are lv 412, mv 414, and rv 416, which represent the amplitude values for the left, middle, and right features respectively. The time values illustrated in FIG. 4B are lp 420, mp 422, and rp 424, which represent time values for the left, middle and right features respectively. For example, the sample amplitude lv 412 of approximately 0.1 mV is detected at a time lp 420 of approximately 21 seconds.

Further processing is illustrated in FIG. 4C. The signal 434 is represented by time series data of sample amplitude 430 (e.g., voltage V) over time 432 (t). As indicated in FIG. 4C, for the noise proxy (cost), the absolute deviation of the signal 434 is accumulated to the smoothed function 436 for a fixed configurable time period 440 (e.g., blackout period). This is divided against the magnitude of the negative deflection.

FIG. 5 illustrates techniques 500 for determining whether a spike is detected. As described above with respect to FIG. 3, the system may determine whether a spike is detected by comparing a set of characteristic values to a corresponding set of threshold values.

FIG. 5 shows values that may be used in the spike identification process. Fit values 501 may include lv 505, lp 508, mv 506, mp 510, rv 504, and rp 512, which represent features in a signal as shown in FIG. 4B. As described at step 310 of FIG. 3, the system may compute a set of characteristic values based on the identified fit values. In some embodiments, the characteristic values ldist 514, rdist 516, ratio, asym, and cost are computed using the equations:

$$ldist = mp - lp \tag{1}$$

$$rdist = rp - mp \tag{2}$$

$$\text{ratio} = \frac{rv}{|mv|} \tag{3}$$

$$asym = \frac{lv}{rv} \tag{5}$$

$$\text{cost} = \frac{esterr}{|mv|}, \tag{6}$$

where ldist is a difference between the second time value and the first time value, rdist is a difference between the third time value and the second time value, ratio is a ratio of the third sample amplitude value and an absolute value of the second sample amplitude value, asym is a ratio of the first sample amplitude value and the third sample amplitude value, and cost is a ratio of an estimated error and the absolute value of the second sample amplitude value. The characteristic values can then be compared to threshold values 530 to determine whether a neural spike is detected (e.g., whether an event is of sufficient likelihood of corresponding to a neural spike in order to transmit the signal for further processing).

As shown in FIG. 5, the system can make the determination whether a spike is detected using a set of logic gates 502 on-chip. The input includes the set of fit values 501: rv 504, mv 506, lp 508, mp 510, and rp 512. The input further includes a set of configurable threshold values—maxasym 518, minratio 520, and maxcost 522, as well as additional configurable threshold values 530: maxldist, minrdist, min_thres, and max_thres. The inputs are used by logic gates to compute characteristic values ldist 514, rdist 516, m1 524, m2 526, and m3 528. Additional values used to determine whether a spike is likely detected include esterr 532, an estimated error value, and thres 534, which may be determined using MAD or standard deviation as described with respect to FIGS. 2 and 10. In some embodiments, the logic gates comprise arithmetic logic units (ALUs) that are implemented using fixed-point arithmetic.

Accordingly, the features identified from the signals are used to determine whether the shape meets a pre-specified criteria for a spike. The criteria may be shared across channels. The threshold values, characteristic values, and fit values are used by logic 540 to determine whether the signal is likely to correspond to a neural spike, in which case the output is_spike 550 is produced. The logic 540 compares the preconfigured threshold values to the characteristic values and the fit values to determine whether there is a sufficient likelihood that a neural spike has been detected.

It should be understood that the above is a specific example of identifying spike shapes using local samples and estimates. Other values can be used to generate estimates which are related to characteristics of the shapes of interest (e.g., first peak height, etc.). The individual samples and their ratios can be used in various ways to obtain such estimates.

Spike Classification

Figure 6:
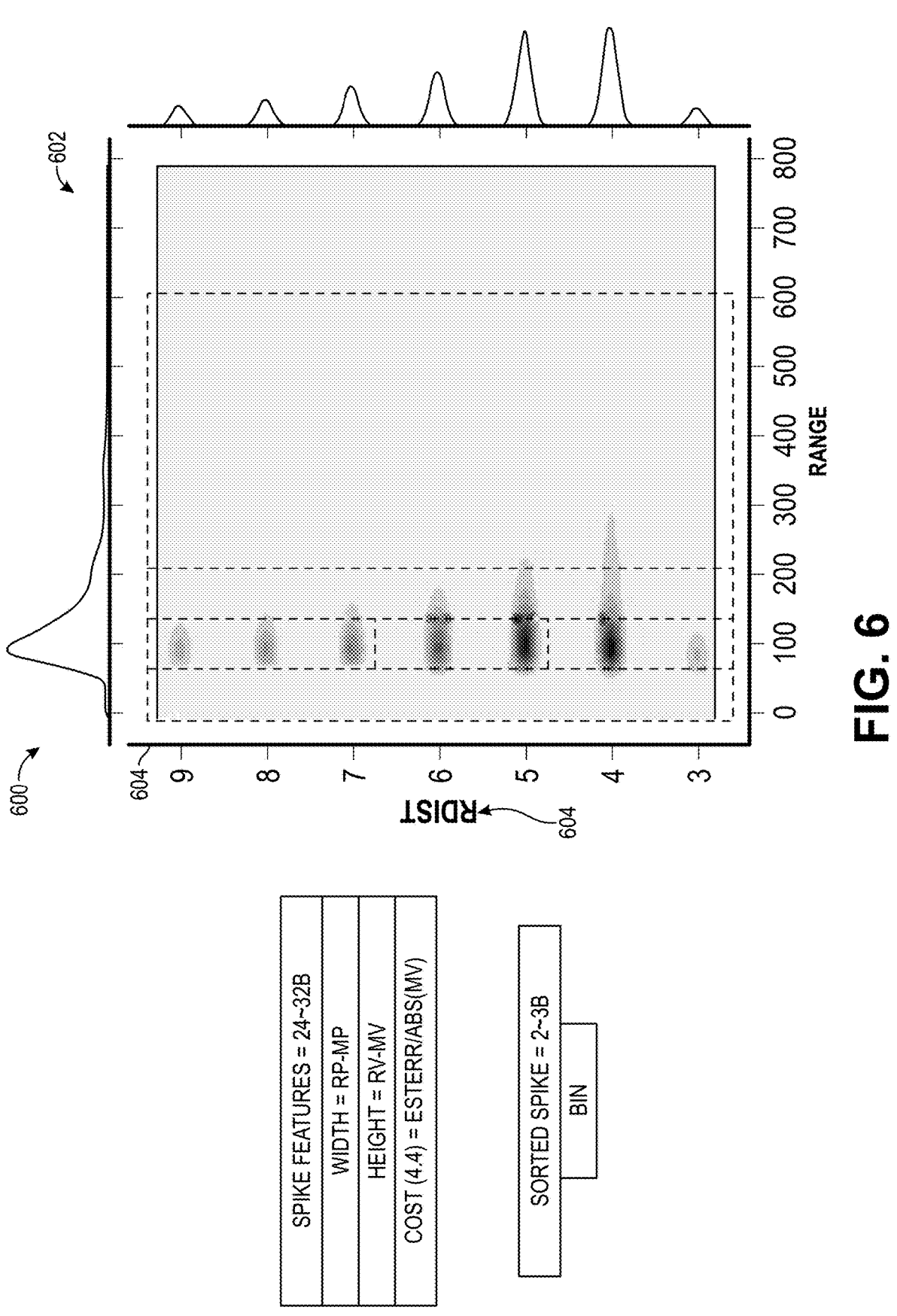
FIG. 6 illustrates techniques for spike classification according to some embodiments.

FIG. 6 illustrates spike classification techniques 600 according to some embodiments. As described above with respect to FIG. 3, in some embodiments, the system may classify a detected signal (e.g., a neural spike) as corresponding to a particular spike category, of a plurality of configured spike categories. Spikes may be classified into a configurable number of classes or types based on bins. For example, each spike may be classified as corresponding to one of four types. As other examples, the spike classes may include five types, six types, eight types, nine types, sixteen types, and so forth.

FIG. 6 shows an example plot 602 where spikes are classified into six bins based on spike features. In the example illustrated in FIG. 6, the spikes are classified based on the value of rdist 604 for each identified spike, i.e., the time between a minimum and maximum voltage value. Alternatively, or additionally, the spikes may be classified based on any one or more fit values and/or characteristic values. For example, the maximum voltage values (e.g., rv) may be used to classify the spikes, the magnitude of the left hump (e.g., lv) may be used to classify the spikes, the relative magnitude of different features may be used to classify the spikes, and so forth.

In some embodiments, an indicator of the classification may be transmitted as a result of the spike analysis. For example, each of the six bins may be assigned a value (e.g., 1, 2, 3, 4, 5, 6), which is transmitted along with a timestamp for the corresponding identified spikes. This information may, for example, be received at a computing device for further analysis. As a specific example, two spikes in two different classifications may be identified as originating from different neurons, one being more distal and/or having different characteristics than the other. Using the spike categories, it can be determined that the signals are different for different neurons, and that can be used to decode useful information. The different neurons could be representing different information, such as a first neuron corresponding to moving a hand up, and a second neuron corresponding to moving a hand down. Simply transmitting an indicator of a bin or category rather than the whole signal or a complex representation of the signal such as a polynomial is advantageous in that it saves processing resources, memory, and time.

Fixed-Point Computation

Figure 7:
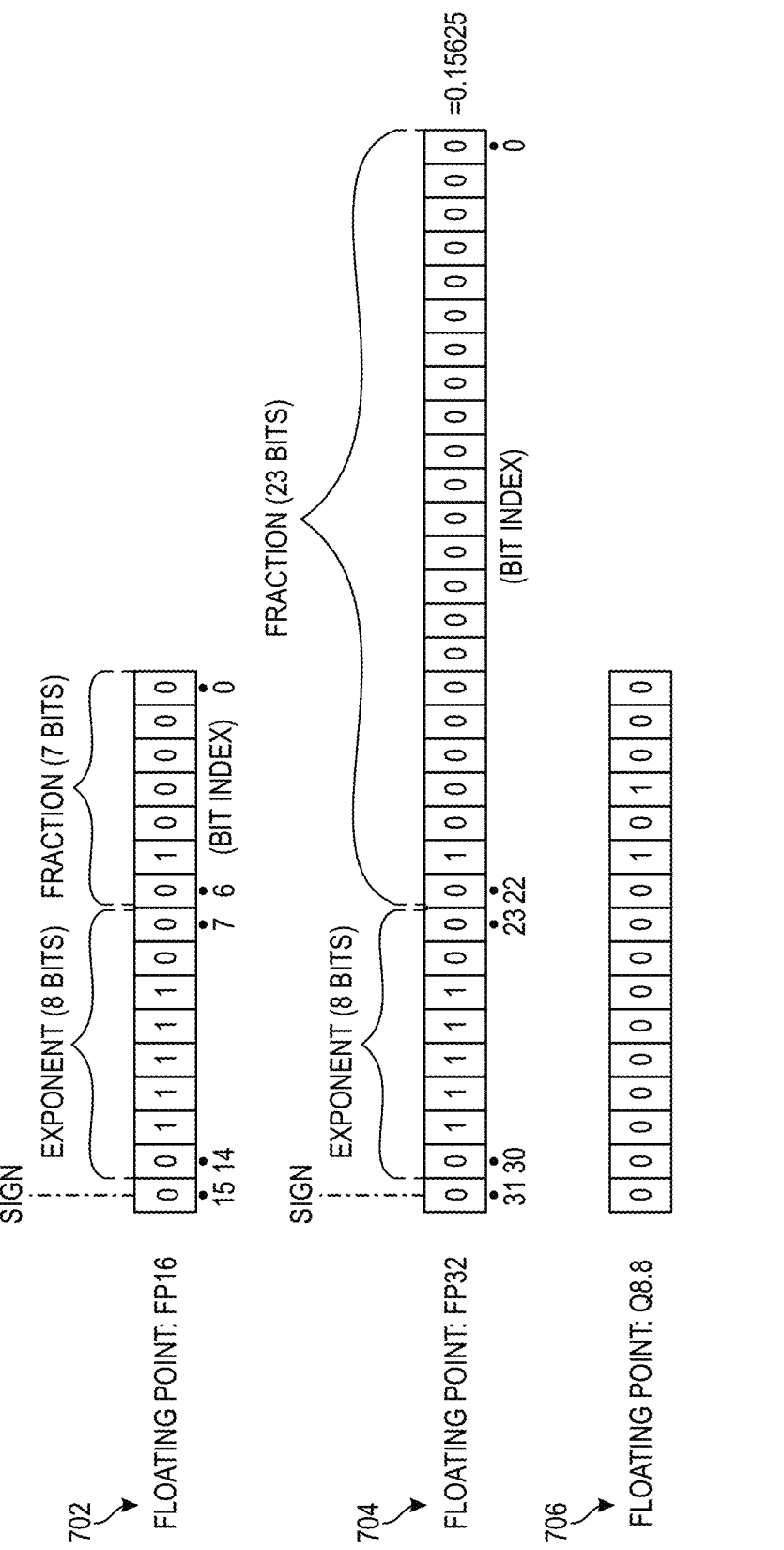
FIG. 7 illustrates number representations according to some embodiments.

FIG. 7 shows a comparison of number representations that can be implemented on a chip such as chip 204 shown in FIG. 2A. A digital signal processor on-chip (e.g., a logical unit for executing mathematical operations) can be implemented using a fixed-point or floating-point number representation. These representations describe the format used to store and manipulate numeric representations of data.

In a floating-point number representation, processing components are designed to represent and manipulate rational numbers via a mantissa and exponent. Floating-point numbers use a minimum of 32 bits, and may use more than 32 bits depending on the specific format used. In FIG. 7, two floating point representations are illustrated—FP16 702 and FP32 704. FP16 702 includes a sign (1 bit), exponent (8 bits), and faction (7 bits), totaling to 16 bits. FP32 704 includes a sign (1 bit), exponent (8 bits), and fraction (23 bits), totaling 32 bits.

In fixed-point representation, processing components are designed to represent and manipulate integers with a fixed number of digits after (and/or before) a decimal point. Fixed-point numbers use a minimum of 16 bits, which varies depending on the specific representation. As illustrated in FIG. 7, Q8.8 representation 706 shows one example of a fixed-point number representation. In the Q8.8 representation 706, eight bits are allocated for an integer portion 708 and eight bits are allocated for a fraction portion 710. As other examples, a Q4.8 fixed-point format allocates 4 bits for integer and 8 bits for fraction, a Q16.8 fixed-point format allocates 16 bits for integer and 8 bits for fraction, and so forth. Using fixed-point representation, math operations can be done using integer arithmetic.

In floating-point computation, the dynamic range is considerably larger than for fixed-point computation. Representing a large dynamic range is particularly desirable when processing large and complex datasets. Additionally, rounding numbers during signal processing can cause quantization error, which is significantly more pronounced in floating-point than in fixed-point. Floating point representation can also be used to avoid overflow issues that tend to occur when using a fixed-point representation. Accordingly, for complex computation such as biological signal analysis, floating-point computation is traditionally used.

However, when pushing spike detection and sorting to the chip, and doing so for hundreds or thousands of channels or more, it becomes important to reduce memory and power needs. Using fixed-point arithmetic instead of the traditional floating-point arithmetic can significantly save such resources, making it possible to identify and sort spikes on-chip for thousands of channels. Fixed-point arithmetic has the advantages of preserving area and latency as compared to floating-point calculations, which is particularly useful in the case of chips implanted in a subject where low power and small size are important. Thus, advantageously, the overall design can be smaller with fixed point-than with floating point. In contrast, floating point math is relatively costly in terms of area and latency. Techniques have been developed, as described with respect to FIG. 8, which can preserve the advantages of fixed-point computation and alleviate the disadvantages.

Figure 8:
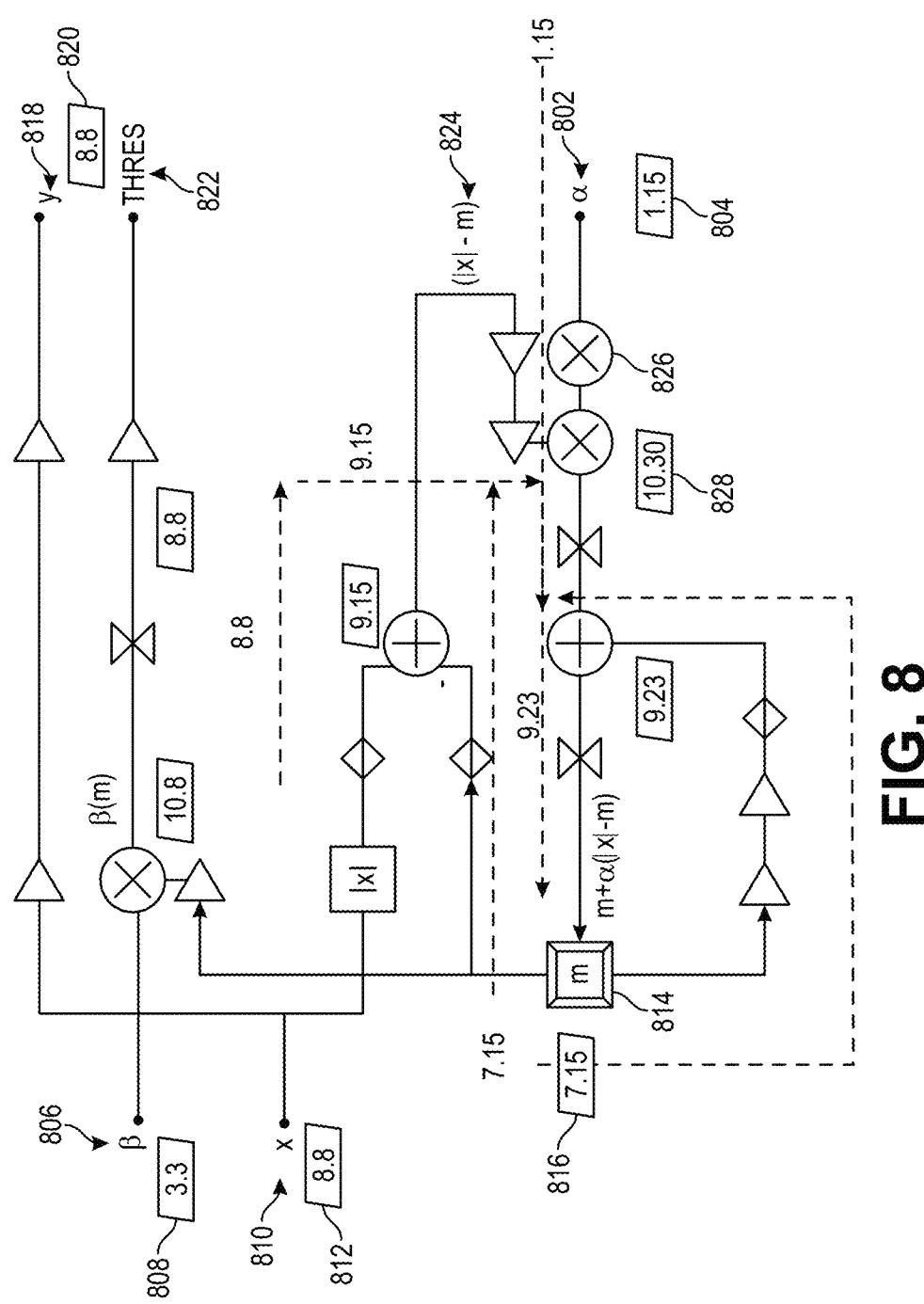
FIG. 8 is a schematic diagram illustrating an implementation of fixed-point number computation according to some embodiments.

FIG. 8 is a schematic diagram 800 illustrating an implementation of a fixed-point computations to preserve resources while maintaining precision, according to some embodiments. In some embodiments, different components are configured with different precisions to spare as many resources and preserve as much accuracy as possible. Fixed-point accuracies may be set to vary between values to minimize use of computational resources—only the necessary bits are used. Where needed (e.g., a small number that will be a divisor), more digits are preserved.

In the example shown in FIG. 8, $\alpha$ 802 is a constant which may be equal to a relatively small number such as 0.0002. As illustrated in FIG. 8, $\alpha$ 802 is represented in as a fixed-point number in Q1.15 format 804 (one bit integer and 15 bits fractional, to precisely represent a very small number). $\beta$ 806 is another constant which may be equal to a larger number (e.g., in the range of approximately 0 to 7.875). $\beta$ 806 is represented as a fixed-point number in Q3.3 format 808 (3 bits integer and 3 bits decimal to represent a larger number). Additional values and their respective number representations are illustrated: x 810 is in Q8.8 format 812, $\hat{m}$ 814 is in Q 7.15 format 816, and y 818 and thres 822 are in Q 8.8 format 820.

In the example illustrated in FIG. 8, various computations are performed on-chip in fixed-point representation. In particular, at 826, $\alpha$ 802 is multiplied by (|x|−m) 824. The output is in Q10.30 representation 828, and is converted to Q9.23 representation at 830. Given that $\alpha$ 802 is a very small number such as 0.0002, multiplying by $\alpha$ 802 creates challenges in fixed-point arithmetic. The challenge of multiplying by 0.0002 is overcome by upscaling and performing 32 b addition. Additional operations (e.g., multiplication (×), addition/subtraction (+), and number representation conversion (hourglass)) are illustrated in FIG. 8. For division, asymmetric multipliers can be used with cycles decided by the smallest operand (16 b). Accordingly, values may be converted from one number representations to another on-chip.

The example illustrated in FIG. 8 shows MAD calculations, which are further described below with respect to FIG. 10. Additionally or alternatively, any or all of the calculations in the spike detection process can be performed using fixed-point arithmetic. For example, computing the set of characteristic values may comprise fixed-point arithmetic calculations. As a specific example, a first characteristic value, of the set of characteristic values, is assigned a first fixed-point number representation (e.g., Q8.8) and a second characteristic value, of the set of characteristic values, is assigned a second fixed-point number representation (e.g., Q7.15), the number representations being different from each other.

Multi-precision Fixed-point arithmetic combined with context specific rounding schemes (RHTE—Round Half To Even, RHTZ—Round Half To Zero) provides accuracy comparable (0.3% overall mismatch) to floating-point implementations, using significantly fewer resources when implemented in hardware (thereby preserving area and power). In some embodiments, the accuracy of the fixed-point apparatus may be confirmed against floating-point models over simulation to optimize the number representations selected. By implementing tailored fixed-point computations as illustrated in FIG. 8, memory and power usage can be reduced by a factor of 10 or more as compared to doing the calculations in floating-point.

Bandpass Filter

FIG. 9 illustrates an example bandpass filter 900 according to some embodiments. As an example, the bandpass filter 900 is a 16-bit digital Infinite Impulse Response (IIR) Butterworth $2^{nd}$ Order Bandpass Filter. The bandpass filter 900 may be programmable.

In some embodiments, the bandpass filter 900 implements the following equations 902:

$$y = xb_0 + w_1 \qquad [7]$$

$$\widehat{w_1} = w_2 + xb_1 - ya_1 \qquad [8]$$

$$\widehat{w_2} = xb_2 - ya_2 \qquad [9]$$

where x 904 is a sample for a channel. y 916 is the output of the filter. $a_1$ 908, $a_2$ 910, $b_0$ 906, $b_1$ 912, and $b_2$ 914 are configurable parameters. These parameters may be set by a user (e.g., using an external computing device coupled to on-chip configuration circuitry as described with respect to FIG. 2A). $w_1$ 918 and $w_2$ 920 are internal states. In some embodiments, $w_1$ 918 and $w_2$ 920 are 16 bits each. In some embodiments, $b_1$=0 and $b_2$=−$b_0$. As shown in FIG. 9, the bandpass calculations can be computed using fixed-point arithmetic operations in a similar fashion as described above with respect to FIG. 8.

The bandpass filter 900 can be used to select a frequency band useful for detecting a particular signal. For example, neural spikes are typically in the 2-3 kHz range. Accordingly, the filter can be used to select a subset of input which includes data in the 2-3 kHz range, along with other factors. The output of the bandpass filter 900 is a filtered signal.

MAD Subsystem

Figure 10:
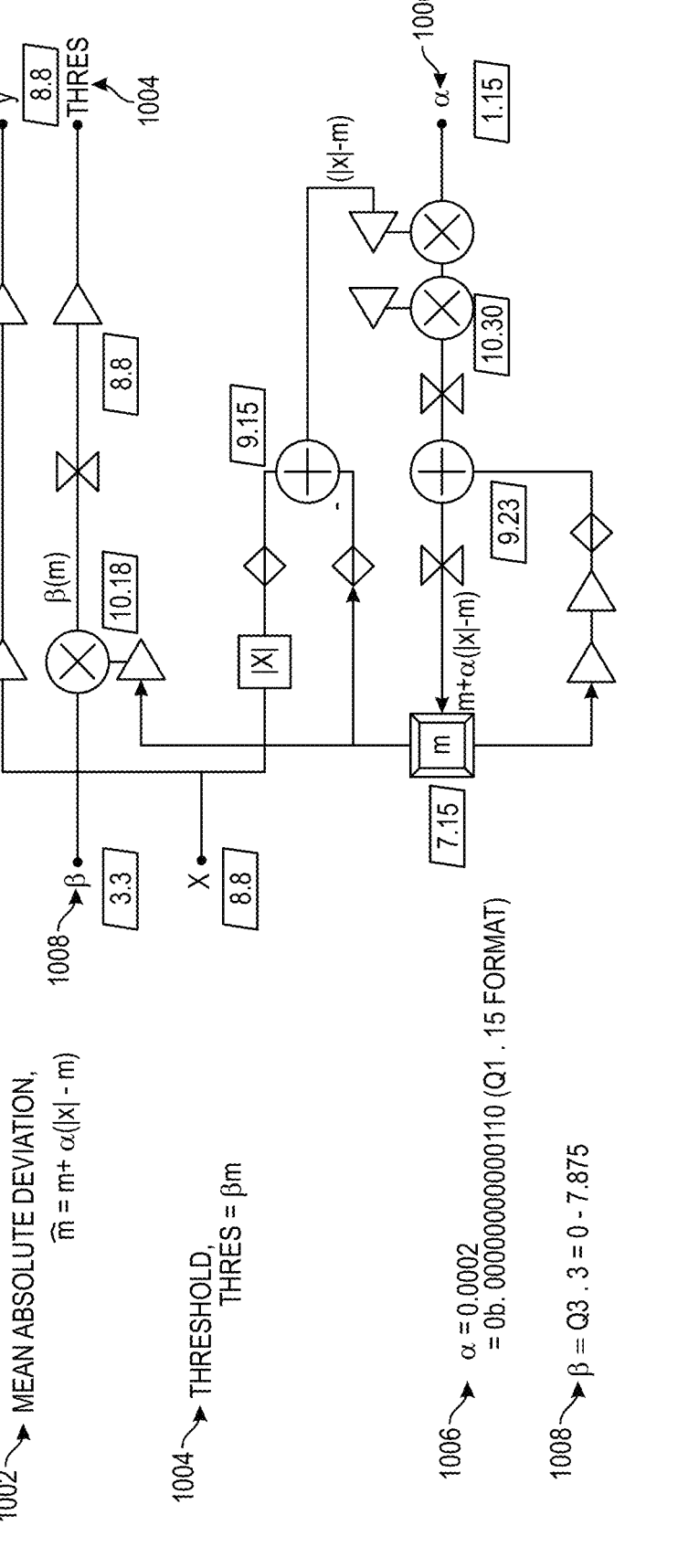
FIG. 10 illustrates determination of mean absolute deviation and related values in accordance with some embodiments.

FIG. 10 illustrates determination of values by the MAD and threshold calculation subsystem 1000 in accordance with some embodiments. Mean Absolute Deviation (MAD) 1002 is an estimate of the statistical dispersion of a channel, and can be used to compute a threshold 1004 used in the spike detection process. MAD 1002 and the threshold 1004 may be computed with the following equations:

$$\hat{m} = m + \alpha(|x| - m) \qquad [10]$$

$$thres = \beta m \qquad [11]$$

where $\hat{m}$ is the MAD estimate, $\alpha$ 1006 is an update multiplier set by the user, $\beta$ 1008 is a scaling factor, and thres is the threshold 1004. In some embodiments, the MAD is accumulated over a 22-bit register in the Q7.15 fixed-point format. Fixed-point computations that may be used in the MAD calculations are further described above with respect to FIG. 8.

The techniques described herein provide multiple advantages. The spike detection methods described above provide a significant reduction in the size of the signal to be retained or transmitted, while maintaining useful information. The spike detection techniques described herein can reduce received waveforms by a factor of 3 orders of magnitude. For example, for 1,000 channels, the data can be reduced from gigabits per second to megabits per second. This facilitates low-power wireless transmission of the compressed data.

Further, the spike detection techniques described herein can be performed significantly faster, and with significantly lower memory and storage requirements, than with prior techniques. Using the techniques described herein, spike detection can be accomplished in near-real time (e.g., roughly 1 μs from the receipt of the signal to determination whether a neural spike is detected). In some embodiments, the system consumes 1-2 milliwatts (mW) per channel or less. For 256 channels, the total system power consumption is under 50 milliwatts (mW), which is significantly less (e.g., 10× or more reduction) than in prior systems.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

The innovations herein may be implemented via one or more components, systems, servers, appliances, other sub-component s, or distributed between such elements. When implemented as a system, such systems may include an/or involve, inter aha, components such as software modules, general-purpose CPU, RAM, etc. found in general-purpose computers. In implementations where the innovations reside on a server, such a server may include or involve components such as CPU, RAM, etc., such as those found in general-purpose computers.

Additionally, the innovations herein may be achieved via implementations with disparate or entirely different software, hardware and/or firmware components, beyond that set forth above. With regard to such other components (e.g., software, processing components, etc.) and/or computer-readable media associated with or embodying the present inventions, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, hand-held or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the innovations herein may be achieved via or performed by logic and/or logic instructions including program modules, executed in association with such components or circuitry, for example. In general, program modules may include routines, programs, objects, components, data structures, etc. that performs particular tasks or implement particular instructions herein. The inventions may also be practiced in the context of distributed software, computer, or circuit settings where circuitry is connected via communication buses, circuitry or links. In distributed settings, control/instructions may occur from both local and remote computer storage media including memory storage devices.

Innovative software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, however no media of any such type herein includes transitory media. Combinations of the any of the above are also included within the scope of computer readable media.

In the present description, the terms component, module, device, etc. may refer to any type of logical or functional software elements, circuits, circuitry and/or processes that may be implemented in a variety of ways. For example, the functions of various circuits and/or circuitry can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the present inventions may be implemented via computer-hardware, software and/or firmware. For example, the network systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

What is claimed is:

1. A method performed by a sensor, including an electrode and a computer chip, implanted in a cranium of a subject, the method comprising:

receiving, by the electrode implanted in the cranium of the subject, a neurological voltage signal, the electrode being connected to an input of the computer chip implanted in the cranium of the subject;

filtering, by bandpass filter circuitry in the implanted computer chip, the received neurological voltage signal to generate a filtered signal;

fitting, by circuitry of the implanted computer chip, the filtered signal to a model;

identifying, by the circuitry of the implanted computer chip, a set of fit values based on the model, the set of fit values comprising a first sample voltage value corresponding to a local minimum voltage value, a second sample voltage value corresponding to local maximum voltage value temporally following the local minimum voltage value; a third sample voltage value corresponding to a local maximum voltage value temporally preceding the local minimum voltage value, a first time value associated with the first sample voltage value, a second time value associated with the second sample voltage value, and a third time value associated with the third sample voltage value;

based on the set of fit values, computing, by the circuitry of the implanted computer chip, a set of characteristic values using fixed-point arithmetic calculation circuitry that uses fewer bits compared to floating-point calculations, wherein the set of characteristic values comprises a difference between the second time value and the first time value, a difference between the third time value and the second time value, a ratio of the third sample voltage value and an absolute value of the second sample voltage value, and a ratio of the first sample voltage value and the third sample voltage value;

comparing, by the circuitry of the implanted computer chip, the set of characteristic values to a corresponding set of threshold values;

based on the comparison, determining, by the circuitry of the implanted computer chip substantially in real time, whether the received neurological voltage signal comprises a neural spike; and based on determining that the received neurological voltage signal comprises the neural spike, transmitting, by a transmitter of the computer chip, an indication of the neurological voltage signal to a receiver remote from the sensor for further analysis, the indication being smaller in size than the received neurological voltage signal, and based on determining that the received neurological voltage signal does not comprise the neural spike, discarding and refraining from transmitting the received neurological voltage signal.

2. The method of claim 1, further comprising:

based on the comparison, classifying the neural spike as corresponding to a spike category, of a plurality of spike categories; and the transmitting step further comprises transmitting an indicator of the spike category and a timestamp.

3. The method of claim 1, wherein the filtering is executed via the bandpass filter circuitry in the computer chip, and the identifying, comparing, and determining steps are executed via a set of logic gates comprised in the computer chip.

4. The method of claim 1, wherein the transmitting step further comprises transmitting, by the transmitter the indication of the neurological voltage signal wirelessly, and wherein the receiver is external to the cranium of the subject.

5. The method of claim 1, further comprising:

based on determining that the received neurological voltage signal corresponds to the neural spike, packetizing and transmitting, by the computer chip, a timestamp corresponding to the neurological voltage signal.

6. The method of claim 1, wherein the computing the set of characteristic values further comprises performing, via dedicated logic circuits of the circuitry of the computer chip, the fixed-point arithmetic calculations.

7. The method of claim 1, wherein the computing further comprises:

assigning a first characteristic value, of the set of characteristic values, a first fixed-point number representation; and assigning a second characteristic value, of the set of characteristic values, a second fixed-point number representation, the number representations being different from each other.

8. The method of claim 1, wherein the receiving the neurological voltage signal further comprises receiving a neural signal via a plurality of electrodes, implanted in the cranium of the subject.

9. A sensor, comprising:

an electrode implantable in a cranium of a subject, the electrode being configured to receive a neurological voltage signal from the cranium of the subject;

a computer chip implantable in the cranium, the computer chip being connected to the electrode and being configured to receive the neurological voltage signal from the electrode, the computer chip including bandpass filter circuitry configured to filter the received neurological voltage signal to generate a filtered signal;

control circuitry configured to:

fit the filtered signal to a model;

identify a set of fit values based on the model, the set of fit values comprising a first sample voltage value corresponding to a local minimum voltage value, a second sample voltage value corresponding to local maximum voltage value temporally following the local minimum voltage value; a third sample voltage value corresponding to a local maximum voltage value temporally preceding the local minimum voltage value, a first time value associated with the first sample voltage value, a second time value associated with the second sample voltage value, and a third time value associated with the third sample voltage value;

based on the set of fit values, compute a set of characteristic values using fixed-point arithmetic calculation circuitry that uses fewer bits compared to floating-point calculations, wherein the set of characteristic values comprises a difference between the second time value and the first time value, a difference between the third time value and the second time value, a ratio of the third sample voltage value and an absolute value of the second sample voltage value, and a ratio of the first sample voltage value and the third sample voltage value;

compare the set of characteristic values to a corresponding set of threshold values;

based on the comparison, determine, substantially in real time, whether the received neurological voltage signal comprises a neural spike; and based on determining that the received neurological voltage signal comprises the neural spike, cause a transmitter of the computer chip to transmit an indication of the neurological voltage signal from the sensor to a receiver that is remote from the sensor for further analysis, the indication being smaller in size than the received neurological voltage signal, and based on determining that the received neurological voltage signal does not comprise the neural spike, discard and refrain from transmitting the received neurological voltage signal; and the transmitter configured to transmit the indication from the sensor to the receiver.

10. The sensor of claim 9, wherein the control circuitry of the computer chip is further configured to:

classify the neural spike as corresponding to a spike category, of a plurality of configured spike categories, based on the comparison, and transmit output comprising an indicator of the spike category and a timestamp.

11. The sensor of claim 9, wherein the transmitter is further configured to transmit the indication of the neurological voltage signal wirelessly, and wherein the receiver is external to the cranium of the subject.

12. The sensor of claim 9, wherein the control circuitry of the computer chip is further configured to, based on determining that the received neurological voltage signal comprises the neural spike, cause the transmitter to packetize and transmit a timestamp corresponding to the neurological voltage signal.

13. The sensor of claim 9, wherein dedicated logic circuits of the control circuitry of the computer chip is further are configured to compute the set of characteristic values using the fixed-point arithmetic calculations.

14. The sensor of claim 9, wherein the control circuitry of the computer chip is further configured to:

assign a first characteristic value, of the set of characteristic values, a first fixed-point number representation; and assign a second characteristic value, of the set of characteristic values, a second fixed-point number representation, the number representations being different from each other.

15. A non-transitory computer-readable media storing a program that, when executed, causes a sensor to perform a method, the sensor including an electrode and a computer chip implanted in a cranium of a subject, the method comprising:

receiving, by the electrode implanted in the cranium of the subject, a neurological voltage signal, the electrode being connected to an input of the computer chip implanted in the cranium of the subject;

filtering, by bandpass filter circuitry in the implanted computer chip, the received neurological voltage signal to generate a filtered signal;

fitting, by circuitry of the implanted computer chip, the filtered signal to a model;

identifying, by the circuitry of the implanted computer chip, a set of fit values based on the model, the set of fit values comprising a first sample voltage value corresponding to a local minimum voltage value, a second sample voltage value corresponding to local maximum voltage value temporally following the local minimum voltage value; a third sample voltage value corresponding to a local maximum voltage value temporally preceding the local minimum voltage value, a first time value associated with the first sample voltage value, a second time value associated with the second sample voltage value, and a third time value associated with the third sample voltage value;

based on the set of fit values, computing, by the circuitry of the implanted computer chip, a set of characteristic values using fixed-point arithmetic calculation circuitry that uses fewer bits compared to floating-point calculations, wherein the set of characteristic values comprises a difference between the second time value and the first time value, a difference between the third time value and the second time value, a ratio of the third sample voltage value and an absolute value of the second sample voltage value, and a ratio of the first sample voltage value and the third sample voltage value;

comparing, by the circuitry of the implanted computer chip, the set of characteristic values to a corresponding set of threshold values;

based on the comparison, determining, by the circuitry of the implanted computer chip substantially in real time, whether the received neurological voltage signal comprises a neural spike; and based on determining that the received neurological voltage signal comprises the neural spike, transmitting, by a transmitter of the computer chip, an indication of the neurological voltage signal to a receiver remote from the sensor for further analysis, the indication being smaller in size than the received neurological voltage signal, and based on determining that the received neurological voltage signal does not comprise the neural spike, discarding and refraining from transmitting the received neurological voltage signal.

* * * * *